US00PP09893P

United States Patent [19]

Walters

[11] Patent Number: Plant 9,893

[45] Date of Patent: May 13, 1997

[54] VARIETY OF GERANIUM NAMED 'JANE'

[75] Inventor: Ernest Walters, deceased, late of Hucknall, England, by Mary Bodill, administrator

[73] Assignee: Oglevee, Ltd., Connellsville, Pa.

[21] Appl. No.: 545,378

[22] Filed: Oct. 19, 1995

[51] Int. Cl.[6] ..... A01H 5/00

[52] U.S. Cl. ..... Plt./87.12

[58] Field of Search ..... Plt./87.12

*Primary Examiner*—Howard J. Locker

*Attorney, Agent, or Firm*—Webb Ziesenheim Bruening Logsdon Orkin & Hanson, P.C.

[57] ABSTRACT

The 'Jane' variety is an improvement over the current Regal variety, 'Peggy' with better rooting time, a more controlled plant habit, improved flower color and better post harvest quality. The inflorescence has a unique light purple/dark purple bi-color appearance above a neat mound of medium green foliage from a distance.

1 Drawing Sheet

BACKGROUND OF THE INVENTION

The present invention comprises a new and distinct cultivar of *Pelargonium ×domesticum* known by the varietal name 'Jane' (Oglevee No. 534, Breeder No. Everbloom II). The new variety was discovered in a selected breeding program in Hucknall, Nottingham, Great Britain in the early to mid 1980's. The parentage of the new variety is not known with certainty but the breeding program of Ernest Walters, deceased, which extended more than 30 years, is disclosed in a Walters article published in vol. 110, Part 8, August 1985, Journal of The Royal Horticultural Society. The new variety was first received in the United States on May 11, 1987 and was asexually reproduced by cuttings at Oglevee, Ltd. in Connellsville, Pa. in Sep. 1, 1987. The new variety was first asexually reproduced by cuttings at Oglevee, Ltd. in Connellsville, Pa. over a several year period. It has also been trial and field tested at Connellsville and has been found to retain its distinctive characteristics through successive propagations.

The cultivar, when grown in a glass greenhouse in Connellsville, Pa. using natural light and temperatures of 60° F. night and 68° F. day, has a response time of fourteen weeks from a rooted cutting to flowering in a 6 inch pot. The response time was determined on plants grown in soilless media employing constant fertilizer 150–200 parts per million of nitrogen and potassium in full light. The rooted cuttings were potted on Nov. 4, 1994 and flowered on Feb. 10, 1995 in a 6 inch pot.

DESCRIPTION OF THE DRAWING

The accompanying photographic drawing illustrates the new cultivar, the colors being as nearly true as possible with color illustrations of this type.

DESCRIPTION OF THE NEW PLANT

The following detailed description sets forth the characteristics of the new cultivar. The data which defines these characteristics were collected by asexual reproductions carried out by Oglevee Ltd. in Connellsville, Pa. The plant history was taken on fourteen week plants blossomed under natural light in a greenhouse and the color readings were taken indoors under 200–220 foot candles of fluorescent cool white light. Color references are primarily to the R.H.S. Colour Chart of The Royal Horticultural Society of London.

THE PLANT

Classification:
- *Botanical.*—*Pelargonium×domesticum.*
- *Commercial.*—Regal geranium.

Form: Upright mound shaped habit.
- *Height.*—20.0–22.0 cm. above media surface.
- *Growth.*—Medium mound shaped habit.

Strength: Neat mound habit so no artificial support is needed, quick rooting.

Foliage: Stalked leaf attachment.

Leaves:
- *Size.*—5.5–8.0 cm across; fully expanded leaf.
- *Shape.*—Depressed ovate; Base: Truncate.
- *Margin.*—Serrately lobed.
- *Texture.*—Leathery, slightly pubescent.
- *Color.*—Top: Yellow-green group 146A. Bottom: Yellow-green group 147B.
- *Ribs and Veins.*—Venation: Palmate. Color: Yellow-green group 147C.
- *Zone.*—N/A.

Petioles:
- *Color.*—Yellow-green group 146B.
- *Length.*2.5–5.5 cm.

Stem:
- *Color.*—Yellow-green group 146C.
- *Internodes.*—1.0–3.0 cm in length.

THE BUD

Shape: Elliptical.

Size: 2.0–3.0 cm across; bud just showing color.

INFLORESCENCE

Blooming habit: Medium size florets forming a full, continuous flower head.

Size:
- *Closed florets.*—1.5–2.0 cm in lenth; 0.5–1.0 cm in width; buds showing small amount of color.
- *Fully open bloom.*—9.0–11.5 cm across.

Borne: Umbel; florets on pedicel; pedicel on peduncle.

Florets:
- *Form.*—Cupped.
- *Color.*—Top: Outer edge, Purple group 75A; Blotch on upper two petals, Greyed-Purple Group 187A; Blotch on lower three petals, Greyed-purple group 187C; All have heavy veining of Greyed-Purple Group 187C atop a background of Purple Group 75A. Bottom: Purple group 75B; veining and blotch showing through a faintly.

*Petals.*—Single, not united; margin entire; 5–6 in number.

*Size.*—5.5–6.5 cm across.

*Texture and appearance.*—Smooth, satiny; appearance from a distance is a unique light purple/dark purple bi-color flower above a neat mound of medium green foliage.

Petaloids:

*Quantity.*—None.

Pedicel:

*Length.*—2.0–3.0 cm.

*Color.*—Yellow-green group 146C.

Peduncle: 4.0–5.5 cm in length.

*Color.*—Yellow-green group 146B.

Disease resistance: Not known.

Lasting quality: Continuous blooming; slow to shatter.

REPRODUCTIVE ORGANS

Stamens:

*Anthers.*—3.0–4.0 mm in length.

*Filaments.*—1.0–1.6 cm in length. Color: Purple group 75D.

*Pollen.*—Golden brown.

Pistils:

*Number.*—1.

*Length.*—1.5–2.0 cm.

*Stigma.*—5 parted; Red-Purple Group 60C.

*Style.*—1.0–1.5 cm in length; Red-Purple Group 60C.

Ovaries: Pubescent; light green; 5.0–7.0 mm in length.

Fruit: None observed.

GENERAL CHARACTERISTICS

The 'Jane' variety is an improvement over the current Regal variety 'Peggy' (U.S. Plant Pat. No. 6,020) with better rooting time, a more controlled plant habit, improved flower color and better post harvest quality.

It is claimed:

1. A new and distinct variety of geranium plant substantially as shown and described.

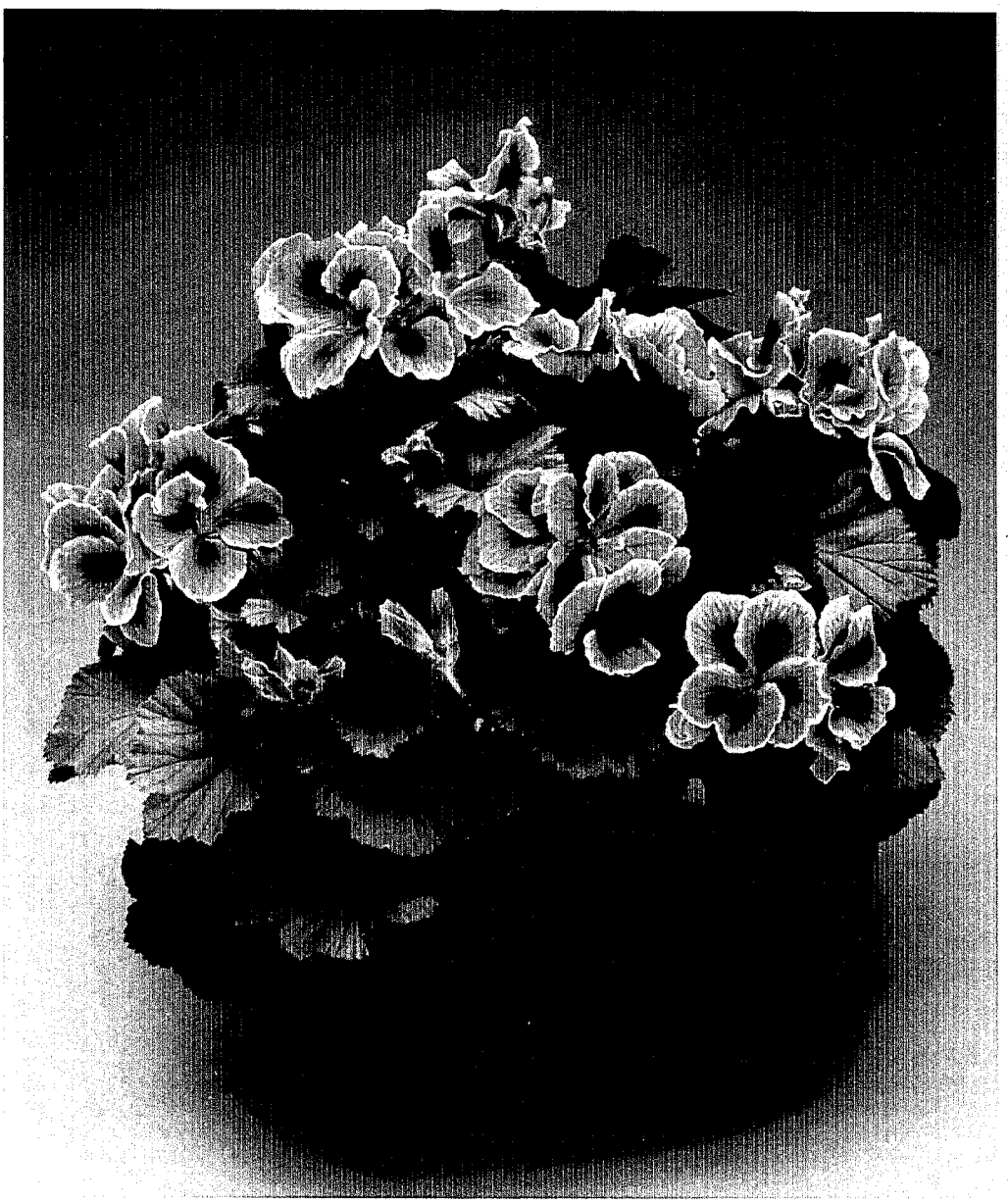

* * * * *